United States Patent
Popovic et al.

(10) Patent No.: US 11,161,248 B2
(45) Date of Patent: Nov. 2, 2021

(54) AUTOMATIC ROBOTIC ARM CALIBRATION TO CAMERA SYSTEM USING A LASER

(71) Applicant: KONINKLIJKE PHILIPS N.V., Eindhoven (NL)

(72) Inventors: Aleksandra Popovic, Boston, MA (US); Johannes Petrus Withagen, Best (NL); David Paul Noonan, New York, NY (US); Jurgen Jean Louis Hoppenbrouwers, Boxtel (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 762 days.

(21) Appl. No.: 15/763,745

(22) PCT Filed: Sep. 14, 2016

(86) PCT No.: PCT/IB2016/055458
§ 371 (c)(1),
(2) Date: Mar. 27, 2018

(87) PCT Pub. No.: WO2017/055955
PCT Pub. Date: Apr. 6, 2017

(65) Prior Publication Data
US 2019/0047151 A1    Feb. 14, 2019

Related U.S. Application Data

(60) Provisional application No. 62/234,102, filed on Sep. 29, 2015.

(51) Int. Cl.
*G05B 19/04*   (2006.01)
*G05B 19/18*   (2006.01)
(Continued)

(52) U.S. Cl.
CPC ........... *B25J 9/1692* (2013.01); *A61B 6/42* (2013.01); *A61B 34/30* (2016.02); *B25J 9/1697* (2013.01);
(Continued)

(58) Field of Classification Search
CPC ...... B25J 9/1692; B25J 11/008; B25J 9/1697; A61B 6/42; A61B 34/30;
(Continued)

(56) References Cited

U.S. PATENT DOCUMENTS

2002/0039183 A1 * 4/2002 Yagita ............... G01N 21/9081
356/240.1
2005/0071047 A1 * 3/2005 Okabayashi ......... G05D 1/0242
700/245
(Continued)

FOREIGN PATENT DOCUMENTS

CN   104197831 A  * 12/2014 ............ B25J 9/1692
DE   102009030883 A1   12/2010
(Continued)

OTHER PUBLICATIONS

"Calibrating Pan-Tilt Cameras in Robot Hand-Eye Systems Using a Single Point" by Chandra Sekhar Gatla, Ron Lumia, John Wood, Greg Starr IEEE International Conference on Robotics and Automation (Year: 2007).*
(Continued)

*Primary Examiner* — Harry Y Oh
*Assistant Examiner* — Sohana Tanju Khayer

(57) ABSTRACT

A system for calibration of a robot includes an imaging system (136) including two or more cameras (132). A registration device (120) is configured to align positions of a light spot (140) on a reference platform as detected by the two or more cameras with robot positions corresponding with the light spot positions to register an imaging system
(Continued)

coordinate system (156) with a robot coordinate system (150).

20 Claims, 3 Drawing Sheets

(51) Int. Cl.
- B25J 9/16 (2006.01)
- A61B 34/30 (2016.01)
- A61B 6/00 (2006.01)
- B25J 11/00 (2006.01)
- G05B 19/4155 (2006.01)

(52) U.S. Cl.
CPC ......... *B25J 11/008* (2013.01); *G05B 19/4155* (2013.01); *A61B 2560/0223* (2013.01); *G05B 2219/37571* (2013.01); *G05B 2219/39022* (2013.01); *G05B 2219/39039* (2013.01); *G05B 2219/40249* (2013.01); *G05B 2219/45169* (2013.01)

(58) Field of Classification Search
CPC ........ A61B 2560/0223; G05B 19/4155; G05B 2219/39022; G05B 2219/37571; G05B 2219/45169; G05B 2219/39039; G05B 2219/40249
See application file for complete search history.

(56) References Cited

U.S. PATENT DOCUMENTS

| | | | |
|---|---|---|---|
| 2006/0063599 A1* | 3/2006 | Greenspan | B25J 9/1697 473/1 |
| 2007/0073439 A1* | 3/2007 | Habibi | G05B 19/4182 700/213 |
| 2008/0181362 A1 | 7/2008 | Gertner | |
| 2010/0131235 A1 | 5/2010 | Aoba | |
| 2015/0025683 A1* | 1/2015 | Amano | B25J 9/1692 700/254 |
| 2015/0230768 A1 | 8/2015 | Belei | |
| 2016/0296293 A1* | 10/2016 | Gill | A61B 90/14 |

FOREIGN PATENT DOCUMENTS

| | | |
|---|---|---|
| EP | 2722136 A1 | 4/2014 |
| GN | 104197831 A | 12/2014 |
| JP | 2001252883 A | 9/2001 |
| JP | 2011011321 A | 1/2011 |
| WO | 2008118198 A2 | 10/2008 |

OTHER PUBLICATIONS

"Calibrating Setups with a Single-Point Laser Range Finder and a Camera" by Thanh Nguyen1 and Gerhard Reitmayr IEEE/RSJ International Conference on Intelligent Robots and Systems (IROS) (Year: 2013).*

Gatla, Chandra Sekhar et al "Calibrating Pan-Tilt Cameras in Robot Hand-Eye Systems using a Single Point", IEEE International Conference on Robotics and Automation, 2007.

* cited by examiner

AUTOMATIC ROBOTIC ARM CALIBRATION TO CAMERA SYSTEM USING A LASER

CROSS-REFERENCE TO PRIOR APPLICATIONS

This application is the U.S. National Phase application under 35 U.S.C. § 371 of International Application No. PCT/IB2016/055458, filed on Sep. 14, 2016, which claims the benefit of U.S. Provisional Patent Application No. 62/234,102, filed on Sep. 29, 2015. These applications are hereby incorporated by reference herein.

BACKGROUND

Technical Field

This disclosure relates to medical instruments and more particularly to a system and method for robot calibration using a camera and a laser.

Description of the Related Art

Interventional imaging systems, such as, an interventional X-ray system, may include cameras in a cover of the X-ray detector. These cameras can be geometrically registered to each other and to the X-ray system. 2D and/or 3D X-ray (e.g., cone bean computed tomography (CBCT)) images from the X-ray system can be overlaid on the camera images. While such a system provides ample imaging information, manual calibration is still needed for performing interventional procedures. Manual calibration can be cumbersome and needs to be performed by trained personnel.

SUMMARY

In accordance with the present principles, a system for calibration of a robot includes an imaging system including two or more cameras. A registration device is configured to align positions of a light spot on a reference platform as detected by the two or more cameras with robot positions corresponding with the light spot positions to register an imaging system coordinate system with a robot coordinate system.

Another system for calibration of a robot includes an X-ray imaging system having an X-ray detector configured to receive X-rays for imaging a subject. A camera array is mounted on the X-ray detector and includes two or more cameras. A robot includes a fixed reference portion and one or more links, such that one link includes a tool holding mechanism, the tool holding mechanism being adjusted to mount a directed light source on a portion of the robot. A registration device is configured to align positions of a light spot on a reference platform as detected by the two or more cameras with robot positions to register an imaging system coordinate system with a robot coordinate system.

A method for calibrating a robot includes projecting a light spot on a reference platform from a robot in at least one known position; imaging the light spot in two or more cameras associated with a medical imaging system; and registering positions of the light spot on the reference platform as detected by the two or more cameras with the at least one known robot positions to register an imaging system coordinate system with a robot coordinate system.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

Figure 1:
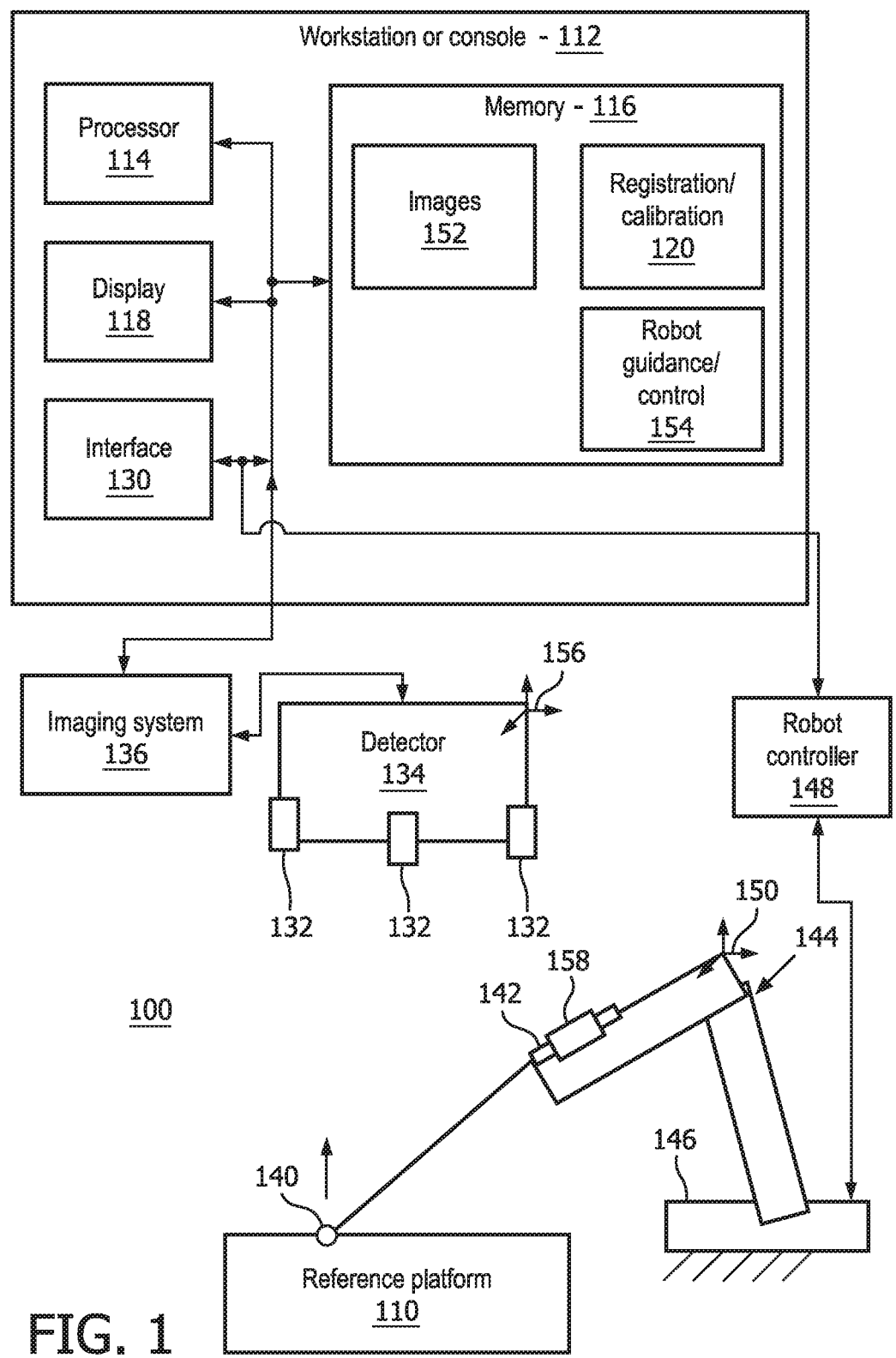
FIG. 1 is a block/flow diagram showing a system for registering a robot to an imaging system in accordance with one embodiment.

In accordance with the present principles, systems and methods for automatic registration/calibration of a robotic arm to a multi-camera system using a laser (pointer) are provided. The laser is coupled to a robot (e.g., on a last stage) and has a known geometry. The robot automatically makes a motion with all joints. This causes the laser pointer to move. The laser light is projected on a flat surface that is visible by a camera system for which the cameras are registered to each other. The cameras record the laser dot or pattern. By using the laser dot's location in several cameras, a 3D position is calculated for the robot. After moving all joints, the robot is registered to the camera system. Some robot control may be achieved using the 3D camera coordinate system. A further benefit includes that the system for registration/calibration may be employed even if robot is not visible in the X-ray or camera system.

In useful embodiments, an automated calibration is provided, e.g., before a procedure or surgery. The automated aspects of the registration/calibration system improve workflow and provide better accuracy. In particularly useful embodiments, a robotic arm may be employed to automatically position instruments or needles at a location and in a direction that is planned on an anatomical volume, e.g., computed tomography (CT) or magnetic resonance (MR) volume. The robotic arm can be mounted anywhere, e.g., a table, floor or ceiling. The robotic arm is registered to the X-ray and/or camera system to permit positioning of the robot using positions and orientations computed with the camera and CT/MRI or other 3D imaging whether or not the robot itself is visible in the X-ray or camera image. In this way, the robot does not obstruct the view.

It should be understood that the present invention will be described in terms of medical instruments; however, the teachings of the present invention are much broader and are applicable to any system using a laser spot or pattern for registration. In some embodiments, the present principles are employed in tracking or analyzing complex biological or mechanical systems. In particular, the present principles are applicable to tracking procedures of mechanical systems for procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

It will also be understood that when an element is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Referring now to the drawings in which like numerals represent the same or similar elements and initially to FIG. 1, a system 100 for registering and/or calibrating a robot to a camera system using a light source is illustratively shown in accordance with one embodiment. System 100 may include a workstation 112 (e.g., a console) from which a procedure is supervised and/or managed. Workstation 112 preferably includes one or more processors 114 and memory 116 for storing programs and applications. Memory 116 may store a registration/calibration module 120 configured to interpret optical images collected by one or more cameras 132. In one embodiment, the cameras 132 are mounted on a detector 134 for an interventional imaging system 136.

The interventional imaging system 136 may include an X-ray system, although other imaging systems may be employed. The detector 134 in this case detects X-ray radiation for imaging a subject on a reference platform 110. The cameras 132 are configured to provide visual feedback from the reference platform 110 for assisting in X-ray imaging, but also to detect a laser spot, spots or pattern 140. While the present principles describe cameras 132 on a detector for the interventional imaging system 136, the imaging system may be any imaging modality including a visual imaging system only (e.g., cameras only).

In accordance with one embodiment, a laser 142 is mounted on a robot 144. It should be understood that laser 142 is a particularly useful light source; however, other light sources may be employed, e.g., a light emitting diode, an intense incandescent source, a light pattern projected on the platform, etc.

The robot 144 preferably includes a fixed mounting point (e.g., a base 146, although other mounting positions may be employed), or a position that includes known coordinates as a reference. In one useful embodiment, the laser 142 is mounted on a last or end link of the robot 144. A robot controller 148 controls the movement of the robot 144 and therefore can provide position and orientation information about every point of the robot 144 relative to a reference location, e.g., using encoders or other measurement systems. The position and orientation information of the robot 144 may be defined in terms of a robot coordinate system 150.

The robot controller 148 may interact with a robot guidance/control system 154 tied into the workstation 112 to permit coordination between the interventional imaging system 136 and the robot 144.

The robot 144 is positioned to permit the light forming the laser spot, spots or pattern 140 from the laser 142 (or other source) to fall incident on the reference platform 110. The cameras 132 can detect this light forming the laser spot, spots or pattern 140 and since there is a plurality of cameras (e.g., two or more), a position of the light forming the laser spot, spots or pattern 140 can be triangulated or stereoscopically determined to estimate the position of the robot 144. Since the relationship between the robot 144 and the laser 142 is known, a camera coordinate system 156 can be registered to the robot coordinate system 150 (or vice versa).

In accordance with one embodiment, an automated procedure is performed to register the robot 144 to a camera reference frame to permit positioning of the robot 144 using positions and orientations computed in by the cameras 132 and CT/MRI or other 3D images 152. This registers the robot 144 without the robot 144 being visible in X-ray or camera images. This improves workflow as the calibration/registration can be performed at any time using the reference platform 110. This can improve workflow as the camera or X-ray line of sight remains unobstructed.

In one embodiment, the robot 144 includes a yaw-pitch robotic arm with an adjustable instrument holding mechanism 158 so that the laser 142 or other light source can be mounted in the adjustable instrument holding mechanism 158. In other embodiments, the laser 142 may be permanently mounted in the robot 144. The camera system comprising one or more 132 may be mounted and may be part of a Philips® Allura Xper™ system or be a separate component. It should be noted that the illustrative description describes a pitch-yaw robot; however, any type of robot and any type of motion may be employed.

Workstation 112 includes a display 118 for viewing images (images 152, preoperative images (CT, MR, etc.), real-time X-ray images, etc.) of the subject (patient) and may include images as overlays on other images (e.g., X-ray images on CT images, etc.). Display 118 may also permit a user to interact with the workstation 112 and its components and functions, or any other element within the system 100. This is further facilitated by an interface 130 which may include a keyboard, mouse, a joystick, a haptic device, or any other peripheral or control to permit user feedback from and interaction with the workstation 112.

Figure 2:
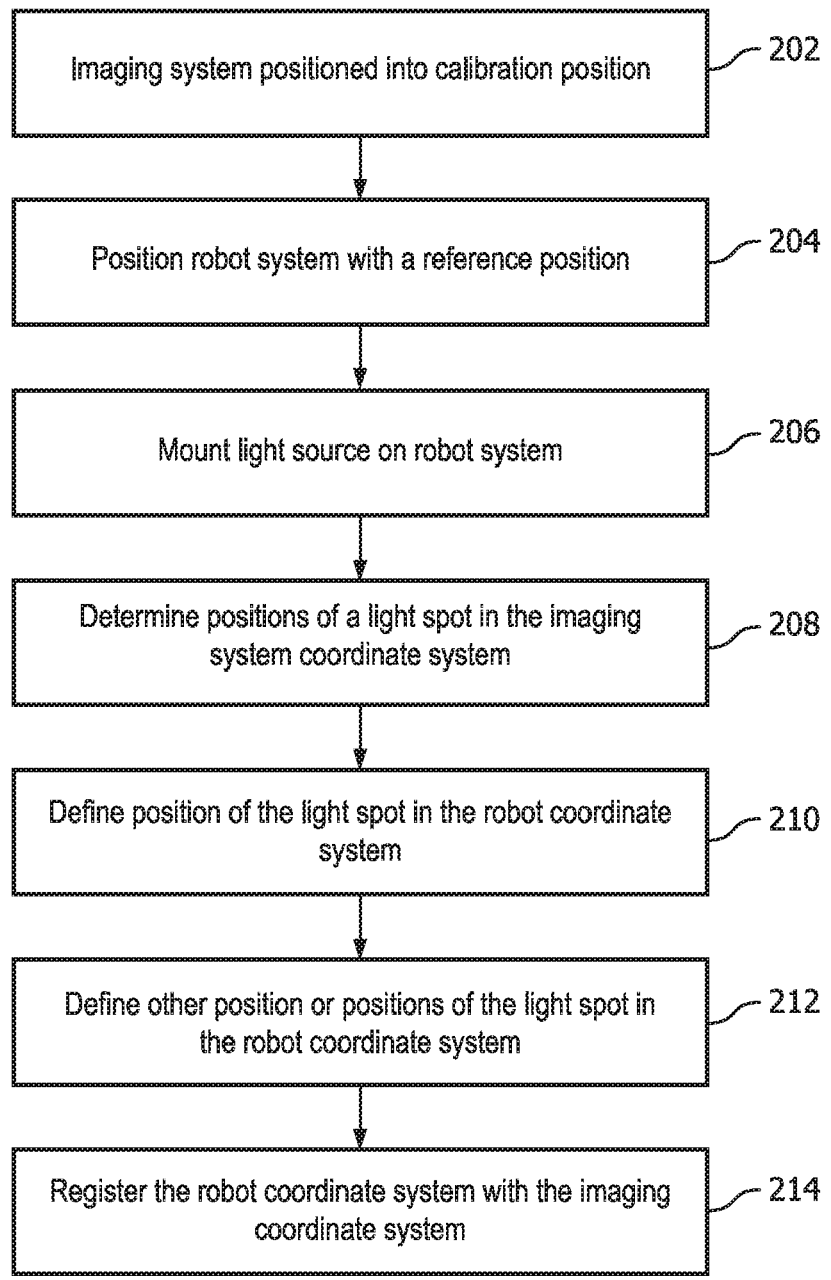
FIG. 2 is a block/flow diagram showing a method for registering the robot to the imaging system in accordance with another embodiment.

Referring to FIG. 2, a method for registering/calibrating a robot to a camera using a laser is illustratively described in accordance with the present principles. In block 202, an interventional imaging (e.g., X-ray) system is positioned into a calibration position (e.g., its "zero" position). In block 204, a robot system is positioned so that a portion (e.g., proximal end portion) of the robot is fixed in space (e.g., in a passive holding arm). In block 206, the robot is equipped with a light source (e.g., a laser pointer). The light source may be temporarily or permanently mounted. The light source projects a dot or pattern on a reference platform, such as, e.g., an operating table. The dot or pattern is visible (imaged) from at least two cameras mounted on a detector (or other location) of the imaging system.

In block 208, using stereoscopic or other geometric methods, a 3D position for each point is known in a coordinate frame for the cameras. In block 210, for the dot or pattern, the robot position is defined. This can be determined by two robot positions in a pitch and yaw system. However, other robot positions may be known using sensors, encoders or other mechanisms for this or other types of robot systems.

In block 212, the robot is moved along a known contour while positions of dots in both coordinate frames (camera and robot frames) are recorded. Instead of moving the robot, multiple light spots (e.g., different colors) may be employed, or a pattern or patterns may be employed for the light spot. In block 214, registration is performed to establish a rigid transformation between the robot coordinate frame and camera coordinate frame.

It is assumed that for each position of the robot during a calibration run, a correspondence between a 3D camera position and robot position is known ($\{x,y,z\} \leftrightarrow$(pitch, yaw) for a pitch and yaw robot linkage), which makes this problem a 3D to 2D registration problem. The pitch and yaw angles can be projected on a plane using a spherical projection.

Figure 3:
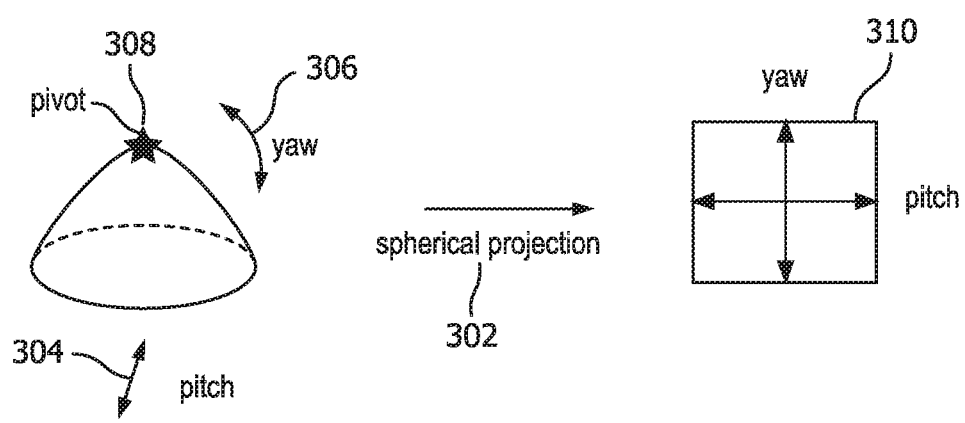
FIG. 3 is a diagram showing a spherical projection for three dimensions to two dimensions for registering a pitch, yaw type robot to an imaging system in accordance with another embodiment.

Referring to FIG. 3, a spherical projection 302 is employed to project pitch angles 304 and yaw angles 306 about a pivot point 308 on a projection plane 310. The size of projection plane 310 (scaling of x and y axis) is a function of distance of the laser dot to a zero position of the robot (pivot point 308 of the robot). Thus, assuming the x-axis is a projection of pitch and y-axis is projection of yaw on projection plane 310, the position of the laser dot on the projection plane 310 is x=d*cos(pitch), y=d*cos(yaw).

The projection of the 3D point in camera coordinates, X1 to robot coordinates is:

$$\begin{bmatrix} x \\ y \\ 1 \end{bmatrix} = d * \begin{bmatrix} \cos(\text{pitch}) & 0 & 0 \\ 0 & \cos(\text{yaw}) & 0 \\ 0 & 0 & 1 \end{bmatrix} * [R\ t] * Xl$$

where R and t are unknown rotation and translations between the imaging (camera) system and the robot system and d is unknown distance between the reference platform and the robot. This projection reduces the problem to a 2D to 3D image projection registration with focal lengths cos(pitch) and cos(yaw) for which various solutions may be employed (e.g., iterative closest point, random sample consensus (RANSAC), etc.).

The present principles permit registration up to a scale ('d') which can be sufficient for any application where the robot is employed to position a tool guide and depth of the tool (such as a needle or drill) is set manually by the surgeon. In further embodiments, if the laser source is not collimated, scale can be retrieved by observing a size of the dot or image. In another embodiment, a grating can be placed in front of the laser, allowing simultaneous calibration without moving the robot.

Figure 4:
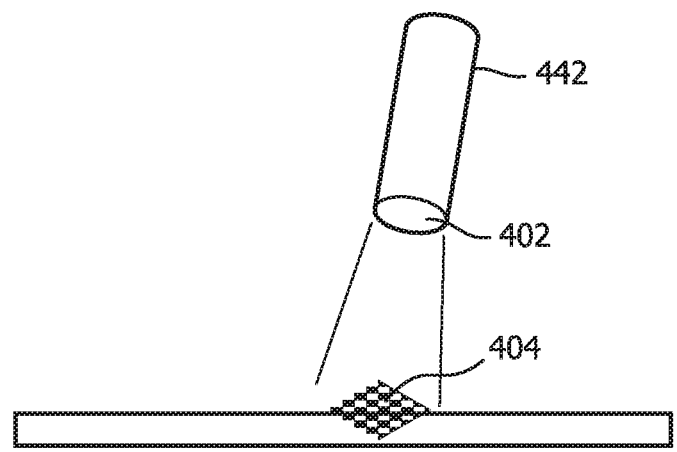
FIG. 4 is a perspective view showing a laser generating a pattern for a light spot in accordance with one embodiment.

Referring to FIG. 4, a light source 442 (e.g., laser) may include a grating or cover 402 for generating a shape pattern or projection 404. The pattern or projection 404 may be employed to indicate the position or orientation of the robot and may be employed to eliminate the need to reposition the robot during calibration/registration. The registration can be repeated more easily during a procedure without significantly disturbing the workflow.

In interpreting the appended claims, it should be understood that:
  a) the word "comprising" does not exclude the presence of other elements or acts than those listed in a given claim;
  b) the word "a" or "an" preceding an element does not exclude the presence of a plurality of such elements;

c) any reference signs in the claims do not limit their scope;
d) several "means" may be represented by the same item or hardware or software implemented structure or function; and
e) no specific sequence of acts is intended to be required unless specifically indicated.

Having described preferred embodiments for an automatic robotic arm calibration to camera system using a laser (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A system for calibration of a robot, the system comprising:
a medical imaging system comprising a detector;
two or more cameras, the two or more cameras being disposed on the detector;
a processor; and
a memory that stores instructions, which when executed by the processor, cause the processor to align a light source mounted on a robot to position a same light spot or pattern on a reference platform as detected by the two or more cameras with robot positions corresponding with the positions of the same light spot or pattern to register an imaging system coordinate system of the medical imaging system with a robot coordinate system.

2. The system as recited in claim 1, wherein the positions of the same light spot or pattern comprises a first light spot or pattern position corresponding to a first position of a robot and a second light spot or pattern position corresponding with a second position of a robot.

3. The system as recited in claim 1, wherein the instructions, when executed by the processor, further cause the processor to generate a rigid transform to correlate the imaging system coordinate system with the robot coordinate system.

4. The system as recited in claim 1, wherein the system is configured so that the robot is not visible by the medical imaging system; and the robot coordinate system is registered to the imaging system coordinate system without view obstruction by a robot.

5. The system as recited in claim 1, wherein the medical imaging system is mounted on an X-ray detector of an X-ray imaging system.

6. The system as recited in claim 1, wherein the same light source comprises a laser pointer.

7. The system as recited in claim 1, further comprising a grating, wherein the light source and the grating are configured to generate the pattern.

8. The system as recited in claim 1, wherein the reference platform comprises an operating table.

9. A system for calibration of a robot, the system comprising:
an X-ray imaging system comprising an X-ray detector configured to receive X-rays for imaging a subject;
a camera array mounted on the X-ray detector and including two or more cameras;
a directed light source adapted to provide a light spot or pattern;
a robot comprising a fixed reference portion and one or more links, wherein one of the one or more links comprises a tool holding mechanism, wherein the tool holding mechanism is adjusted to mount the directed light source on a portion of the robot;
a processor; and
a memory that stores instructions, which when executed by the processor, cause the processor to align positions of the light spot or pattern on a reference platform as detected by the two or more cameras with robot positions to register an imaging system coordinate system with a robot coordinate system.

10. The system as recited in claim 9, wherein the positions of the light spot or pattern comprises a first light spot or pattern position corresponding to a first position of the robot and a second light spot or pattern position corresponding with a second position of the robot.

11. The system as recited in claim 9, wherein the instructions, when executed by the processor, further cause the processor to generate a rigid transform to correlate the imaging system coordinate system with the robot coordinate system.

12. The system as recited in claim 9, wherein the system is configured so that the robot is not visible by the X-ray imaging system; and the robot is registered to the imaging system coordinate system without obstructing a view of the X-ray imaging system.

13. The system as recited in claim 9, wherein the directed light source comprises a laser pointer.

14. The system as recited in claim 9, wherein the directed light source comprises a grating to generate a pattern for the light spot.

15. The system as recited in claim 9, wherein the reference platform comprises an operating table.

16. A method for calibrating a robot, comprising:
projecting a light spot or pattern on a reference platform from the robot in at least one known position;
imaging the light spot or pattern in two or more cameras associated with a medical imaging system, wherein the two or more cameras are disposed on the medical imaging system; and
registering positions of the light spot or pattern on the reference platform as detected by the two or more cameras with the at least one known position to register an imaging system coordinate system with a robot coordinate system.

17. The method as recited in claim 16, wherein the positions of the light spot include a first light spot or pattern position corresponding to a first position of a robot and a second light spot or pattern position corresponding with a second position of a robot.

18. The method as recited in claim 16, further comprising generating a rigid transform to correlate the imaging system coordinate system with the robot coordinate system.

19. The method as recited in claim 16, wherein registering includes registering the robot coordinate system to the imaging system coordinate system without view obstruction by the robot.

20. The method as recited in claim 16, wherein the light spot includes a pattern.

* * * * *